(12) United States Patent
Amitai et al.

(10) Patent No.: US 10,092,202 B2
(45) Date of Patent: Oct. 9, 2018

(54) MINIATURE ECG DATA ACQUISITION DEVICE

(71) Applicants: David Amitai, Ramat Gan (IL); Assaf Amitai, Paris (FR)

(72) Inventors: David Amitai, Ramat Gan (IL); Assaf Amitai, Paris (FR)

( * ) Notice: Subject to any disclaimer, the term of this patent is extended or adjusted under 35 U.S.C. 154(b) by 341 days.

(21) Appl. No.: 13/710,886

(22) Filed: Dec. 11, 2012

(65) Prior Publication Data
US 2014/0163349 A1    Jun. 12, 2014

(51) Int. Cl.
*A61B 5/0408* (2006.01)
*A61B 5/00* (2006.01)
*A61B 5/0404* (2006.01)
*A61B 5/0432* (2006.01)
(Continued)

(52) U.S. Cl.
CPC ........ *A61B 5/04085* (2013.01); *A61B 5/0006* (2013.01); *A61B 5/0022* (2013.01); *A61B 5/0404* (2013.01); *A61B 5/04028* (2013.01); *A61B 5/0432* (2013.01); *A61B 5/6826* (2013.01); *A61B 5/6893* (2013.01); *A61B 5/7203* (2013.01); *A61B 5/7475* (2013.01); *A61B 5/117* (2013.01); *A61B 5/6823* (2013.01); *A61B 5/6843* (2013.01); *A61B 5/6898* (2013.01); *A61B 5/747* (2013.01); *A61B 2503/22* (2013.01);
(Continued)

(58) Field of Classification Search
CPC . A61B 5/0402; A61B 5/0404; A61B 5/04028; A61B 5/6893; A61B 5/0006; A61B 5/0022; A61B 5/0024; A61B 5/0452

USPC ................................... 600/509, 393; 607/60
See application file for complete search history.

(56) References Cited

U.S. PATENT DOCUMENTS

| 5,505,202 A | 4/1996 | Mogi |
|---|---|---|
| 5,876,351 A | 3/1999 | Rohde |

(Continued)

FOREIGN PATENT DOCUMENTS

JP    3417049 B2    6/2003

OTHER PUBLICATIONS

International Search Report dated Apr. 8, 2014, PCT/IL2013/000090.
(Continued)

*Primary Examiner* — Alyssa M Alter
(74) *Attorney, Agent, or Firm* — Calvin B. Ward

(57) ABSTRACT

An apparatus for generating ECG recordings and a method for using the same are disclosed. The apparatus includes a handheld device having four electrodes on an outer surface thereof, the handheld device having an extended configuration and a storage configuration. The apparatus also includes a controller configured to measure signals between the electrodes to provide signals that are used to generate an ECG recording selected from the group consisting of standard lead traces and precordial traces. When the handheld device is in the extended configuration and the first and second electrodes contact a first hand of a patient such that the first and second electrodes contact different locations on the first hand, the third electrode is in contact with a location on the patient's other hand and the fourth electrode contacts a point on the patient's body that depends on the particular trace being measured.

18 Claims, 9 Drawing Sheets

(51) Int. Cl.
    *A61B 5/0402*     (2006.01)
    *A61B 5/117*     (2016.01)

(52) U.S. Cl.
    CPC ............ *A61B 2560/0418* (2013.01); *A61B 2560/0425* (2013.01); *A61B 2560/0468* (2013.01)

(56) References Cited

U.S. PATENT DOCUMENTS

| | | | | |
|---|---|---|---|---|
| 6,083,248 | A * | 7/2000 | Thompson | A61B 5/0031 607/30 |
| 6,480,744 | B2 * | 11/2002 | Ferek-Petric | A61N 1/37258 128/903 |
| 6,842,722 | B2 * | 1/2005 | David | A61B 5/4041 128/846 |
| 7,433,718 | B2 * | 10/2008 | Manabe et al. | 455/575.1 |
| 2004/0048605 | A1 * | 3/2004 | Schaefer et al. | 455/414.2 |
| 2006/0018200 | A1 * | 1/2006 | Pitocco | G04G 11/00 368/223 |
| 2008/0243021 | A1 * | 10/2008 | Causevic | A61B 5/0002 600/544 |
| 2009/0112112 | A1 | 4/2009 | Lee | |
| 2010/0076331 | A1 * | 3/2010 | Chan | A61B 5/0006 600/522 |
| 2011/0125040 | A1 | 5/2011 | Crawford | |

OTHER PUBLICATIONS

Preliminary Report of Patentability dated Jun. 25, 2015, PCT/IL2013/000090.

* cited by examiner

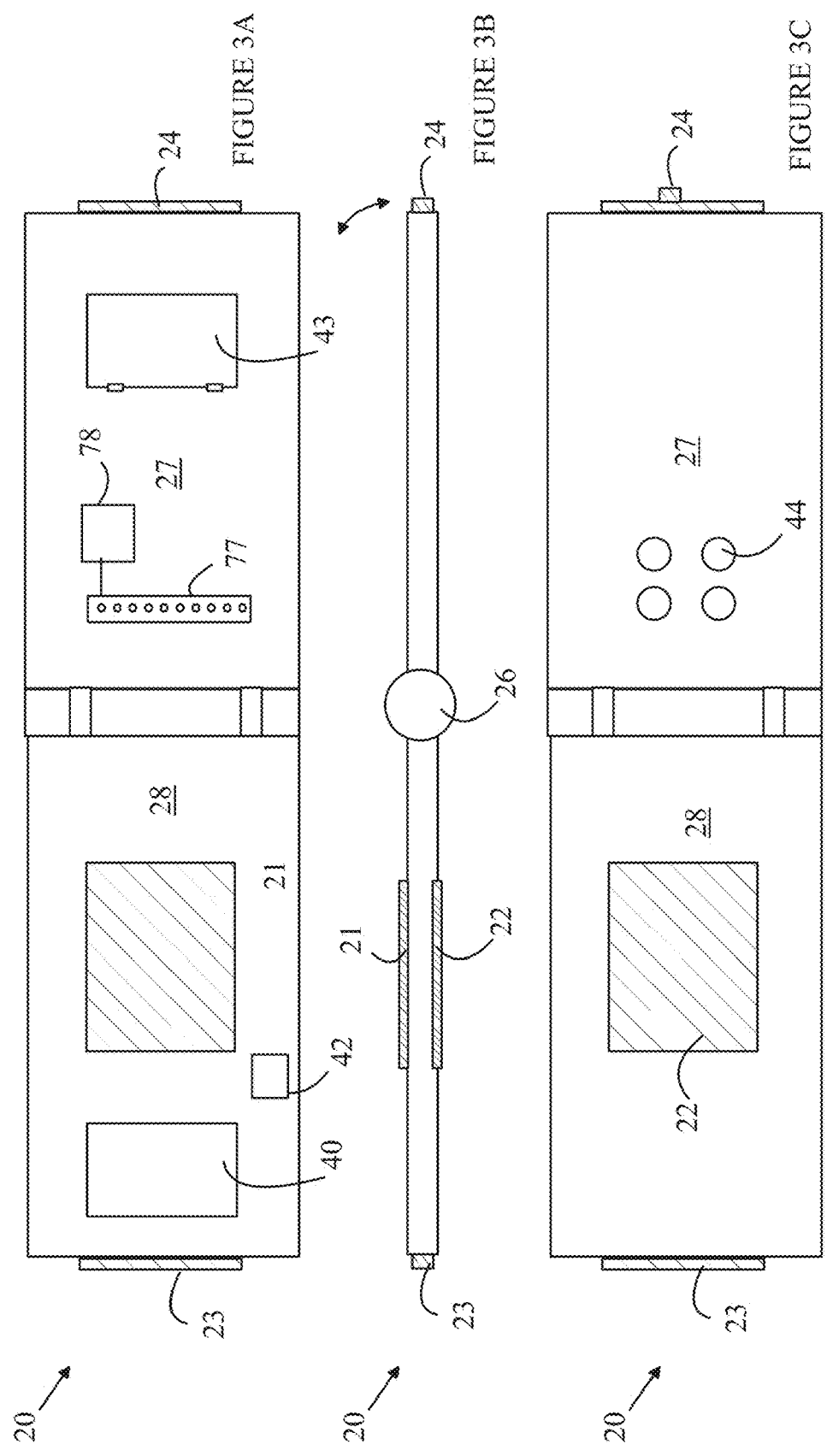

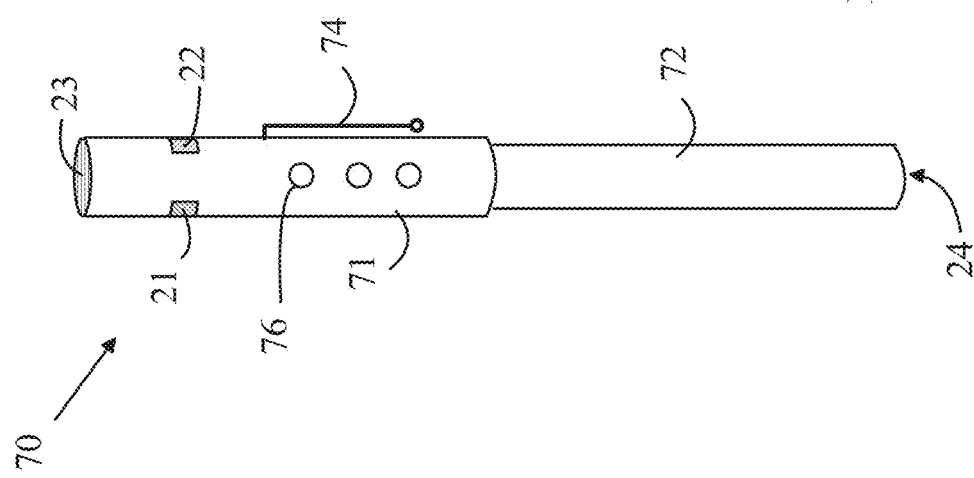

MINIATURE ECG DATA ACQUISITION DEVICE

CROSS REFERENCE TO RELATED APPLICATIONS

This is a Continuation-in-Part of co-pending U.S. patent application Ser. No. 13/293,888 filed Nov. 10, 2011, which is a Divisional of U.S. patent application Ser. No. 12/191, 923 filed on Aug. 14, 2008, now issued as U.S. Pat. No. 8,082,025B2 issued on Dec. 20, 2011. Both of these prior applications are hereby incorporated by reference in their entirety.

BACKGROUND OF THE INVENTION

ECG measurements are a standard form of cardiac measurement for assessing the condition of a patient's heart. Physicians are trained to interpret a standard set of ECG recordings that are normally obtained by connecting ten electrodes to the patient's body and measuring the voltages between various electrodes and combinations of electrodes as a function of time.

While the standard measurements are easily obtained in a medical setting, such measurements pose challenges when a patient is not in such a setting, which is most of the time. A patient with heart problems would benefit both from a clinical and psychological point of view if the patient could measure the standard set of recordings when symptomatic to determine if the recordings had changed since they were last measured. If the recordings were within the expected range, the patient would be reassured and could go about his or her normal activity. If the measurements were outside the expected range, the patient could transmit them to the patient's physician, the physician could interpret the measurements and advise the patient accordingly or, the measurements can be transmitted automatically to a pre-defined medical entity.

A number of systems for making measurements outside of the clinical setting have been proposed. These systems include some form of ECG electrodes that are attached to the patient's body and connected to a local processor carried by the patient. The local processor typically includes a transmitter that relays the measurements from the unit worn by the patient to a physician at a remote location. The relay mechanism can utilize a telephone line, either land or cellular, or some form of dedicated transmitter.

The systems that duplicate the standard measurements require that electrodes be attached to the patient's body. To provide a full 12 lead ECG recording set, electrodes are typically attached to the patient's upper and lower limbs, as well as to a number of locations on the torso. If the patient is in a setting in which the patient has only limited mobility, such a set of attached electrodes may be acceptable; however, if the patient is fully mobile and attending to his or her normal routine outside of a medical environment, temporary or permanent attachment of the electrodes is not usually acceptable and involves a fair amount of discomfort. Furthermore, the electrodes must be removed when the patient bathes. Hence, some arrangement is needed in which the patient or a caregiver places the electrodes on the patient's body at the time an ECG is to be recorded. A system based on the use of adhesively coated electrodes such as those utilized in normal ECG measurements presents problems from a logistical and cost point of view. The individual electrodes are only usable for a small number of measurements before the adhesive fails. Furthermore, the repeated placement and removal of the electrodes can cause patient discomfort, particularly in patients having body hair in the areas to which the electrodes must be attached. In addition, the patient is often incapable of connecting the electrodes to his or her body at all of the required locations.

Hence, a system that can be utilized by the patient without the help of trained personnel would be advantageous. One such system is discussed in the above-identified co-pending patent application. In that system, a handheld device with four electrodes on the surface thereof is used to generate the 12 standard measurements. The four electrodes are used in various combinations to contact the body at locations that the user can easily reach. By making measurements between various electrodes and various contact points, a good approximation to the conventional 12 standard measurements can be obtained. The device is connected to a communication device that can be used to transmit the data to medical personnel.

The size of this and other portable devices still presents challenges. The above-described device is integrated into a cellular telephone or other form of personal data device. However, it would still benefit from a significant reduction in size so that the device would be no more cumbersome to carry than a USB memory module.

SUMMARY

The present invention includes an ECG data acquisition device and method for using the same. The ECG data acquisition device includes a handheld device having first, second, third, and fourth electrodes on an outer surface of the handheld device, the handheld device having an extended configuration and a storage configuration. The ECG data acquisition device also includes a controller that measures signals between the electrodes and provides those signals to another device to generate an ECG recording selected from the group consisting of standard lead traces and precordial traces. When the handheld device is in the extended configuration and the first and second electrodes contact a first hand of a patient such that the first and second electrodes contact different locations on the first hand, the third electrode is in contact with a location on the patient's other hand and the fourth electrode contacts a point on the patient's body chosen from the group consisting of the patient's lower abdomen, one of the patient's legs, and a precordial measurement point on the patient, the point depending on the ECG recording. The ECG data acquisition device also includes a circuit that generates a common mode cancellation signal from signals on the second, third, and fourth electrodes and couples the common mode cancellation signal to the first electrode while the controller is measuring said signals.

In one aspect of the invention, the ECG data acquisition device includes a wireless communication link that transmits the measured signals to a device that is external to the handheld device.

In another aspect of the invention, the handheld device in the storage configuration is too small to allow the patient to contact the first, second, third, and fourth electrodes in a manner that allows the ECG recordings to be made.

In another aspect of the invention, the handheld device includes a compartment for storing medication, the compartment opening in response to signals from the controller.

BRIEF DESCRIPTION OF THE DRAWINGS

FIGS. 3A-3D illustrate one embodiment of an ECG data acquisition device according to the present invention.

FIG. 7 illustrates another embodiment of an ECG data acquisition device according to the present invention.

DETAILED DESCRIPTION OF THE PREFERRED EMBODIMENTS OF THE INVENTION

Figure 1:
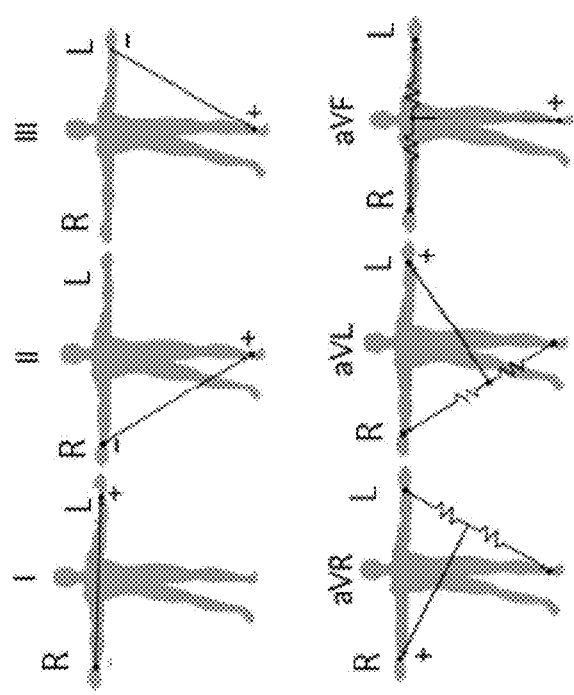
FIG. 1 illustrates the placement of electrodes and the signals that are measured in the "standard lead measurements" that are six of the 12 recordings provided in a conventional 12 lead ECG.

The manner in which the present invention provides its advantages can be more easily understood with reference to FIG. 1, which illustrates the placement of electrodes and the signals that are measured in the "standard lead measurements" that are six of the 12 recordings provided in a conventional 12 lead ECG. The standard lead measurements provide recordings as a function of time of the potentials between pairs of electrodes that are connected to the patient's body. For example, the first standard lead measurement, which is often referred to as the lead I measurement, or just Lead I, consists of the difference in potential measured between the left and right wrists of the patient, as a function of time. Similarly, the lead II measurement, or Lead II, consists of the difference in potential, as a function of time, measured between the left leg and the right wrist of the patient. Lead III consists of the difference in potential, as a function of time between the left leg and the left wrist of the patient. The remaining three leads, aVR, aVL, and aVF are differences between the potential of one limb and the average potential of another two limbs Denote the potential at the right wrist or hand by $\Phi_r$, the potential at the left wrist or hand by $\Phi_l$, and the potential the left leg by $\Phi_f$. The first three standard leads or traces are given by $$I=\Phi_l-\Phi_r,$$

$$II=\Phi_f-\Phi_r, \text{ and}$$

$$III=\Phi_f-\Phi_l=II-I \quad (1)$$

As noted above, these signals are each functions of time. In the following discussion, the Lead I signal as a function of time will be referred to as the hand signal. The Lead II signal as a function of time will be referred to as the leg signal.

Three additional traces are generated by utilizing weighted sums and differences of the Lead I and II signals, namely $$aVR=\Phi_r-(\Phi_l+\Phi_f)/2=-(I+II)/2,$$

$$aVL=\Phi_l-(\Phi_r+\Phi_f)/2=I-II/2, \text{ and}$$

$$aVF=\Phi_f-(\Phi_r+\Phi_l)/2=II-I/2. \quad (2)$$

Figure 2:
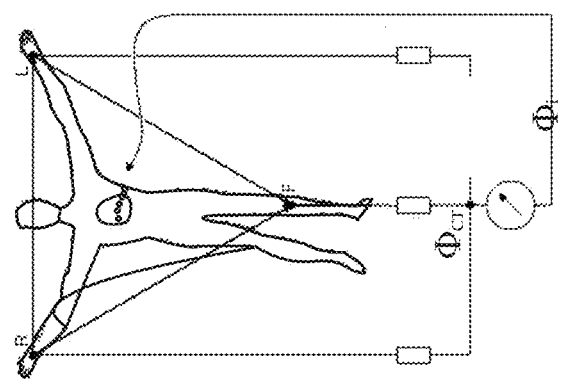
FIG. 2 illustrates the measurement of the precordial traces.

The remaining six traces of the conventional 12 lead ECG are the precordial traces ($V_1$-$V_6$). Refer now to FIG. 2, which illustrates the measurement of the precordial traces. In the conventional precordial measurements, each trace is generated by forming the average of the potentials at the right and left wrists and the left leg (this averaged potential is known as Wilson's Central-Terminal $\Phi_{CT}$) and then measuring the difference between a potential, $\Phi_i$, detected by an electrode at a corresponding point on the patient's chest and $\Phi_{CT}$. A different predetermined point on the chest is used for each of the six traces:

$$V_i\Phi_i-(\Phi_l+\Phi_f+\Phi_r)/3=\Phi_i-\Phi_{CT}, \quad (3)$$

where $V_i$ (i=1 . . . 6) are the precordial leads. The average signal from the hands and leg is often referred to as the "C-terminal". It should be noted that a C-terminal signal can be generated from other locations on the three extremities in question. For example, the potentials corresponding to the leg can be measured at the foot, ankle, or upper thigh or lower abdomen. Similarly, the potentials corresponding to the "hands" can be measured any place between one of the fingers and the shoulder.

It should be noted that the traces are always measured as a difference in potential between two electrodes placed on the corresponding locations on the patient's body by utilizing differential amplifiers to form the differences of the signals in question. Ideally, this procedure eliminates the effects of common mode signals that are picked up by the patient's body such as the 50 or 60 cycle AC signals that are present in most indoor environments. Unfortunately, the magnitudes of the common mode signals are much greater than that of the heart signals that are the subject of the measurements in question, and the available differential amplifiers have a common mode rejection figure that is insufficient to eliminate all of the common mode noise in question.

To reduce the common noise, a signal that is a good approximation to a signal that would cancel the common mode signal in the patient's body is generated and then injected into the right ankle in conventional ECG measurement devices. This signal will be referred to as the common mode cancellation signal in the following discussion. The common mode cancellation signal must be injected at a location that will not interfere with the measurement of the signals from the ECG electrodes. The common mode cancellation signal reduces the common mode signal in the patient's body by canceling the common mode signal that is picked up from the patient's body, and hence, reduces the problems associated with the large difference between the common mode noise and the signals of interest, since the signals of interest no longer have a large common mode signal as part of each signal.

In the prior art, an electrode attached to the right ankle is used as the injection point for the common mode cancellation signal. This does not present a significant problem with respect to the signals detected by the other electrodes, since the right ankle is far from the location of the other electrodes, and hence, any localized signal variations are dissipated by the time the cancellation signal reaches the portions of the body near the electrodes of interest. Since the C-terminal signal is an average of the potentials at widely separated points on the patient's body, the inverse of the C-terminal signal is often utilized as the common mode cancellation signal. That is, the inverse of the C-terminal signal is injected into the right ankle to reduce the common mode noise.

Figure 3D:
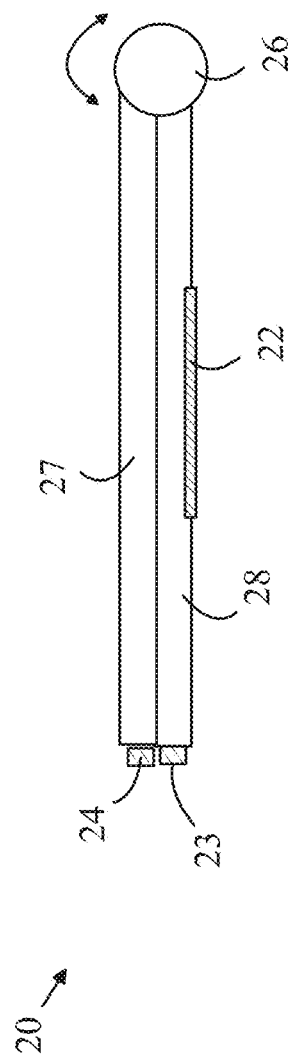

The present invention is based on the observation that a good approximation to the conventional 12 lead ECG measurements can be obtained by using a handheld probe that has four electrodes on the outer surface of the probe. Refer now to FIGS. 3A-3D, which illustrate one embodiment of an ECG data acquisition device according to the present invention. ECG data acquisition device 20 has an extended configuration and a storage configuration. FIG. 3A is a top view of ECG data acquisition device 20 in the extended configuration; FIG. 3B is a side view of ECG data acquisition device 20 in the extended configuration, and FIG. 3C is a bottom view of ECG data acquisition device 20 in the extended configuration. FIG. 3D is a side view of ECG data acquisition device 20 in the storage configuration, which in the case of ECG data acquisition device 20 is a folded configuration. When being used to measure ECG recordings, ECG data acquisition device 20 is operated in the extended configuration. For storage, ECG data acquisition device 20 is folded. In one embodiment, the ECG data acquisition device measures less than 7 cm in the folded configuration.

It should be noted that providing a very small object that is carried by the user when not being used is important. If the object is large, the user will not carry it with the user. A device that is the size of a memory stick when in the storage configuration can easily be accommodated on a key chain or the like. Hence, the user is not inconvenienced by having the device with the user at all times. In one aspect of the invention, the ECG data acquisition device includes one or more buttons such as button 44 that are used for providing user inputs into the ECG data acquisition device. These buttons can be used by the user to signal the ECG data acquisition device that the user wishes to perform a specific measurement such as one particular ECG recording.

In addition, these buttons can be used to input data that is not related to the ECG measurements. As noted above, providing a device that is small enough to encourage the user to carry the device with the user at all times is an important consideration. To the extent that the ECG data acquisition device can provide some other function that the user would like, the other function increases the probability that the user will have the ECG data acquisition device with the user when a suspected cardiac event is occurring. In one aspect of the invention, the ECG data acquisition device also serves the function of an electronic key. For example, the user could input a code to the ECG data acquisition device through the buttons that causes the ECG data acquisition device to utilize its wireless link to perform some function such as an electronic key for an automobile or a garage door opener. Hence, the ECG data acquisition device can also replace an electronic key that the user would normally carry thereby increasing the probability that the user would have the ECG data acquisition device when needed. In this regard, it should also be noted that the ECG pattern of one Lead I trace is known to vary from person to person, and hence, this pattern can be used as a biometric key that enables the key function in question.

While the keypad function described above is implemented using separate keys, it should be noted that the function could be implemented using a touch-enabled display such as display 40. The preferred method for inputting the required data depends on the available power. The keypad requires less power. In addition, electronic car keys typically have a few buttons to provide the functions on the key, and hence, the user is familiar with the button implementation.

Figure 4:
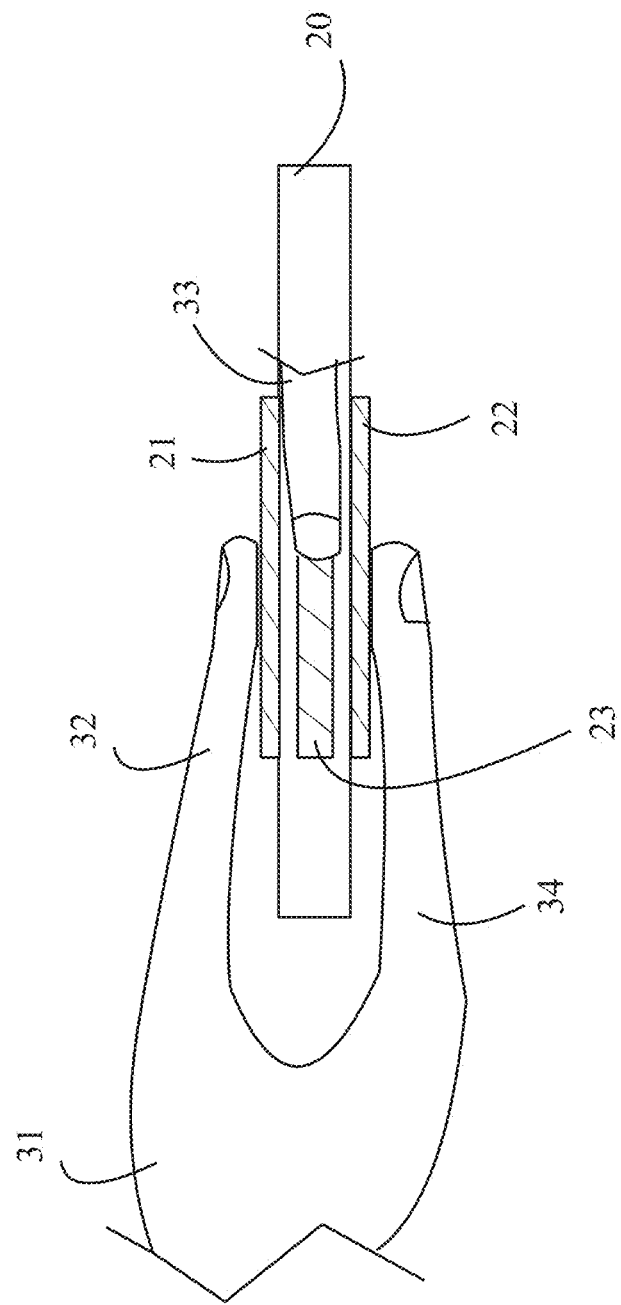
FIG. 4 is an end view of one embodiment of an ECG data acquisition device according to the present invention when the device is gripped by the user.

Referring to FIGS. 3A-3C, ECG data acquisition device 20 includes four electrodes shown at 21-24, respectively. A 12 trace ECG diagram is obtained using ECG data acquisition device 20 by holding the ECG data acquisition device with both hands and pressing electrode 24 against the appropriate place on the patient's body. Refer now to FIG. 4, which is an end view of ECG data acquisition device 20. In one embodiment, electrodes 21 and 22 are held in the right hand 31 with the thumb 32 on electrode 21 and the right index finger 34 on electrode 22. The left index finger 33 or any part of the left palm is held on electrode 23. It should be noted that electrode 22 can be touched with other fingers of the right hand besides the index finger. Electrode 21 can also be touched with other fingers or part of the right hand. Referring again to FIGS. 3A-3C, for the standard lead measurements, electrode 24 is placed against any point of the left leg or the lower abdomen. For the precordial measurements, electrode 24 is placed sequentially at each of the precordial positions on the patient's chest.

As noted above, the four conventional electrodes are placed on the left and right wrists and the left and right ankles. In the present invention, these measurements are provided by using the potential at the right index finger, i.e., electrode 22, in place of the potential at the right wrist, the potential at the right thumb, i.e., electrode 21 in place of the potential at the right ankle, the potential at the left index finger, i.e., electrode 23, in place of the potential at the left wrist, and the potential at the left leg, i.e., electrode 24 in place of the potential at the left ankle.

The common mode cancellation signal is injected into the right thumb through electrode 21 in this embodiment of the present invention. It has been observed that using the thumb for the common mode cancellation signal injection site provides the desired cancellation of the common mode noise without significantly interfering with the measurements of the ECG recordings even though the signal from the right index finger is used to generate the ECG recordings. It should be noted that using another finger on right hand for the injection of the signal has been found to provide more interference with the recordings than the use of the thumb. Accordingly, the thumb is preferred. In addition, using the thumb and index finger to grip the electrodes provides a more comfortable operating position then using another location on the right hand.

The above-described embodiments are optimized for a right-handed user. However, the device can equally be utilized by a left-handed user. When used by a left-handed user, thumb and index finger of the left hand contact electrodes 21 and 22 and the user touches electrode 23 with a finger or thumb of his or her right hand. It should also be noted that the common mode rejection signal can be injected into the index finger that is contacting electrode 22 and the measurements made through the thumb that contacts electrode 21. The specific arrangement can be set in the software that is downloaded to the ECG data acquisition device and customized to the particular user.

In the present invention, the common mode cancellation signal is derived from the sum of the signals from electrodes 22, 23 and 24 denoted by $\Phi_{22}$ $\Phi_{23}$ and $\Phi_{24}$ respectively. During the standard lead measurements, the common mode cancellation signal is analogous to the conventional common mode cancellation signal, as it corresponds to the C-terminal signal. During the precordial measurements, the chest signal is recorded on electrode 24. However, it has been found experimentally, that the resultant common mode cancellation signal is still sufficient to provide the necessary level of common mode signal reduction.

Figure 5:
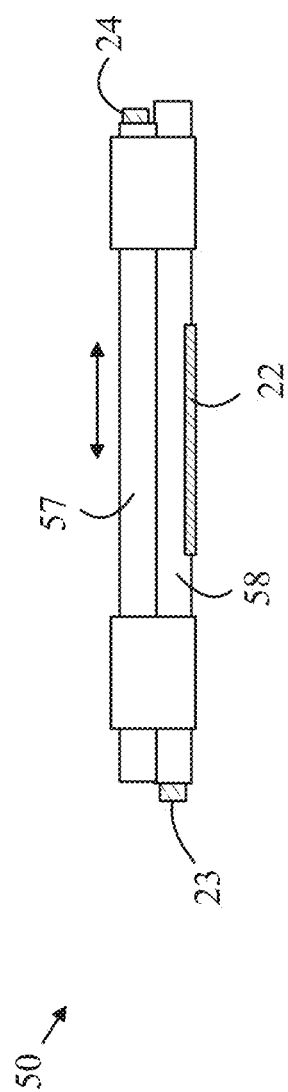
FIG. 5 is a side view of an ECG data acquisition device in a storage configuration after the two sections have been moved relative to one another for storage.

ECG data acquisition device 20 is constructed from sections 27 and 28 that are hingedly connected by hinge 26. However, other arrangements in which the two sections move apart by sliding with respect to one another for use during measurements could be utilized. Such an arrangement is shown in FIG. 5, which is a side view of an ECG data acquisition device 50 in a storage configuration after the two sections shown at 57 and 58 have been moved relative to one another for storage.

In one aspect of the invention, the extended configuration provides three electrodes that are spaced apart sufficiently to allow the electrodes to be contacted with a finger of one hand and two fingers of the other hand and still provide a fourth electrode that can be placed at various locations on the patient's body while the patient is holding the device with the fingers contacting the electrodes. While making measurements, it is important that the user's hands from the wrist up to the armpits do not touch any part of the bare torso or other bare body part, as such contact would alter the effective electrical path from the heart to the wrists. If any other part, such as the barehanded forearm touches the bare torso, or bare leg, the ECG readings could be altered and would not represent the true signals derived from the heart.

In one aspect of the invention, the distance between electrode 24 and the group electrodes 21, 22 and 23 in the extended configuration is set such that the user is forced to lift the user's elbows to the side, thus positioning the user's arms away from the user torso or leg. The length of the extension in the extended configuration is used to maintain the required arm placement. In another aspect of the invention, the present invention is provided with extensions of different lengths to accommodate variations in body types and sizes between various users. The extensions can telescope into one another such that the extensions do not significantly increase the size of the device when the device is placed in the storage configuration even with the longest extension. The telescopic extension increases the distance between electrodes 24 and the group of electrodes 21, 22 and 23.

In the storage configuration, the device is more compact than in the extended configuration. That is, the user could not hold the device with the fingers so contacting the electrodes and the fourth electrode being available for contacting the other points on the patient's body. In one aspect of the invention, the device has a maximum dimension of less than 7 cm in the storage configuration and opens up to a device that has a maximum dimension greater than 12 cm. The minimum sized device in the measurement configuration must be large enough to accommodate two fingers gripping electrodes 21 and 22 and be long enough to place electrode 24 against the various locations at which recordings are to be made without the arms or hands coming in contact with the torso of the patient.

Refer now to FIG. 7, which illustrates another embodiment of an ECG data acquisition device according to the present invention. ECG data acquisition device 70 is configured to resemble a pen and sized to fit in the user's pocket in a manner analogous to the manner in which a pen is clipped into a pocket. In this case, clip 74 provides the clip function. ECG data acquisition device 70 includes a first section 71 that includes electrodes 21-23 and a bottom section 72 that includes electrode 24. Section 72 can move into section 71 to provide a more compact device in the storage configuration. In some cases, the movement of section 72 into section 71 may not be needed. For example, a device that has a length of a conventional pen may function adequately for individuals with a range of body types. For individuals that are overweight a longer device may be needed, and hence, the ability to extend the length is desirable.

ECG data acquisition device 70 also includes one or more LEDs such as LED 76 that are utilized to signal the user as to the next operation to be performed when making measurements. Clip 74 can also act as a release for moving or locking sections 71 and 72 with respect to one another. It should also be noted that embodiments in which clip 74 provides the function of one of the hand electrodes could also be constructed.

It should be noted that for some users, the length of the pen in the storage configuration may be sufficient to provide the spacing function discussed above during measurements. Hence, ECG data acquisition device 70 is configured to be operative for making measurements in both the storage configuration and the extended configuration. The two sections of ECG data acquisition device 70 can include a spring mechanism that causes the sections to move to the extended configuration when clip 74 is pushed. While the conversation between the storage and extended configuration utilizes clip 74 in the embodiment shown in FIG. 7, other release mechanisms could be utilized.

The size of the device in the extended configuration can be advantageously increased for making measurements on persons with limited flexibility such as elderly persons. In such cases, a device that is larger and more easily grasped may be preferred.

In one aspect of the invention, the ECG data acquisition device includes the electronics for providing the signals corresponding to the I, II, and an approximation to $V_i$. The device also generates the signal equal to the inverse of the potentials on electrodes 22-24 and couples that signal to electrode 21. The approximation to $V_i$ is given by $$V_i - \Phi_i - (\Phi_l + \Phi_r)/2 = \Phi_i - \Phi'_{CT} \qquad (4)$$

The common mode cancellation signal is $$V_{21} = -(\Phi_{22} + \Phi_{23} + \Phi_{24})/3 \qquad (5)$$

Figure 6:
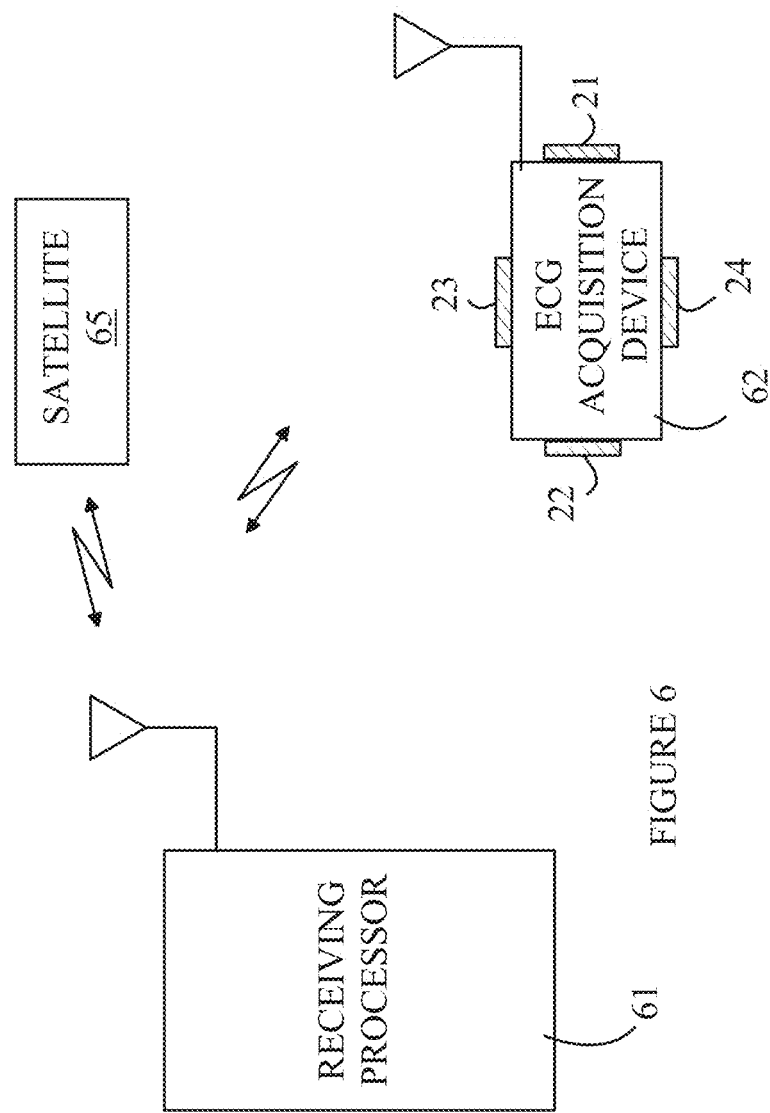
FIG. 6 illustrates the relationship between an ECG data acquisition device according to one embodiment of the present invention and a receiving processor.

In one aspect of the invention, the ECG data acquisition device transmits signal values for I, II, and $V_i$ as a function of time via a wireless link to a receiving processor. Refer now to FIG. 6, which illustrates the relationship between an ECG data acquisition device according to one embodiment of the present invention and a receiving processor. A receiving processor is defined to be any computational device with sufficient computational capacity to compute the 12 conventional ECG recordings from these signals. The receiving processor 61 could be a portable device that the user also carries with the user or a fixed device within range of the wireless link. For example, these signals can be transmitted to a receiving processor 61 comprising smart phone, personal data assistant (PDA), tablet computer, or laptop personal computer via Bluetooth, WiFi, or other wireless communication link. If the user is within range of a PC or other non-portable computer, that computer could also be used as the receiving processor. The computational capacity of the receiving processor is used to construct the ECG recordings. Since the precordial measurements are provided one at a time, the receiving processor 61 also provides signals that are displayed on the ECG data acquisition device 62 to signal the user as to the next contact point for the fourth electrode. Refer again to FIG. 3A. In one aspect of the invention ECG data acquisition device 20 includes a display 40 that displays the signals from the receiving processor as well as status signals generated by ECG data acquisition device 20 itself. The display can be implemented as a series of LED lights with one light indicating the appropriate location for the fourth electrode in the current measurement.

It should be noted that splitting the ECG recording between the ECG data acquisition device and the receiving processor makes a small ECG data acquisition device possible, since the ECG data acquisition device does not need to include the additional electronics for processing the signals to ECG recordings and for transmitting that information to a third party when necessary. In addition to reducing the electronics, the functional split also reduces the size of the battery needed to power the ECG data acquisition device, which, in turn, also makes a smaller ECG data acquisition device possible. As noted above, limiting the size of the ECG data acquisition device is critical to ensuring that the device will be with the patient when the patient perceives that the patient may be having a cardiac event. In one embodiment, the receiving processor provides the display functions of display 40 discussed above. However, embodiments in which the various functions are split in a different manner between the ECG data acquisition device and the receiving processor can also be constructed.

In practice, the user signals the receiving device or the receiving processor that the user is ready to make set of ECG recordings. This signal can be generated by a button on the ECG data acquisition device or by the act of moving the ECG data acquisition device from storage configuration to the extended configuration. If the display on the receiving processor is used for this function, the user signals the receiving processor, which sends the appropriate signals to the ECG data acquisition device.

The receiving device then initializes the relevant application on the receiving device and sends a command that activates one of the LEDs. The user then touches the corresponding three electrodes with the user's fingers and places the fourth against the user's body at the indicated location. When ECG data acquisition device 20 detects that all of the electrodes are in contact with the user, ECG data acquisition device 20 begins transmitting the relevant signals to the receiving processor. The signals can be sent as analog signals or digitized by an analog to digital converter with ECG data acquisition device 20 and sent as digital signals. When the receiving processor has received sufficient data for the signal in question, the receiving processor signals the user by activating another LED or causing the ECG data acquisition device to make an audible signal using an acoustical signal generator 42. The receiving processor then activates another LED that signals the user to move to the next position for the fourth electrode.

The division of the computational labor between the ECG data acquisition device and the receiving device can be adjusted to reflect the amount of electronics that can be conveniently placed in the ECG data acquisition device and the desired battery life of the ECG data acquisition device on a single charge of its batteries. In embodiments that have greater computational capacities, the ECG data acquisition device can perform most, if not all, of the computational activities. In such embodiments, the receiving device is used as a relay to a remote site that may include medical personnel, and, optionally, as a more extensive display screen than can be conveniently placed on the ECG data acquisition device without the space constraints of the ECG data acquisition device in the storage configuration.

It should be noted that the preferred mode of communication between the ECG data acquisition device and the receiving processor can depend on other functions provided by the ECG data acquisition device. As noted above, embodiments in which the ECG data acquisition device serves some additional function such as an electronic key are advantageous in ensuring that the ECG data acquisition device is carried by the user. The frequencies utilized in providing these other functions are typically set by the functions in question. For example, the frequencies with which an electric key for use in a keyless ignition system in an automobile operate are set by the car manufacturer and are not necessarily one of the frequencies used in wireless communications for computer systems. Hence, an ECG data acquisition device that is to provide this additional frequency must provide a communication link that operates at that the dual use frequency. The ECG data acquisition device also needs to communicate with the receiving processor, which may use a different frequency or frequencies for its wireless communications.

In one aspect of the present invention that operates with such dual use ECG data acquisition devices, the receiving processor is modified to use the dual use frequency rather than providing two separate frequencies in the ECG data acquisition device. This reduces the power consumption and complexity of the ECG data acquisition device. It is typically easier to equip the receiving processor with a separate communication channel that is used to communicate with the ECG data acquisition device than to add a second frequency to the ECG data acquisition device, since, the receiving processor typically has fewer power constraints than the ECG data acquisition device.

Refer again to FIG. 6. It should be noted that the receiving processor could be a processor that provides a network interface to another processor or processors. For example, the ECG data acquisition device could communicate with the processor in a vehicle that is connected to satellite service 65 that provides emergency and other services. The satellite server is typically linked to a computer network. To simplify the drawings, the links between the satellite server and the computer network have been omitted. Such services automatically call for emergency vehicles when the air bags are deployed in a car. The GPS receiver in the car provides the location of the car having the problem. In this case, the ECG data acquisition device could communicate on the existing Blue Tooth link in the car that is used for connecting to cellular telephones, and other electronic devices. A patient in the car who has concerns can then perform an ECG and communicate the results to the automobile computer. The automobile computer could process the results and inform the patient of the results or just communicate the results to a central processor at the satellite service. The satellite service could provide processing and/or a relay service to send the results to an appropriate medical site.

Utilizing the automobile's ability to act as the receiving processor is particularly advantageous in that the automobile can communicate by satellite even in areas that lack cellular telephone service. In addition, the patient could be receiving an ECG in route to a hospital so that the results are forwarded to the hospital ahead of the patient's arrival.

The above-described embodiments utilize wireless communications for coupling the ECG data acquisition device to the receiving processor. This wireless link can also be used for downloading updated software or user specific information such as a reference ECG. In one aspect of the invention, a multi-purpose connector is also supplied for connecting the ECG data acquisition device to a receiving processor for transmitting control signals or other communications to the ECG data acquisition device and for charging the batteries in the ECG data acquisition device by connecting the ECG data acquisition device to a suitable charging device. Refer again to FIG. 3A. A connector 77 is optionally included in the ECG data acquisition device. Connector 77 is configured to accept a plug that has a set of ten conventional ECG electrodes for recording a conventional 12 trace ECG that is administered by a third party on the patient. In addition, connector 77 also accepts a cable having a conventional computer communication link such as a USB communication link. Connector 77 utilizes this conventional communication link to charge the batteries in ECG data acquisition device 20 as well as download information such as software updates and/or patient specific information. While connector 77 is shown at a specific location on ECG data acquisition device 20, connector 77 can be located at other points.

In one aspect of the invention, a controller 78 in the ECG data acquisition device recognizes the different possible mating connectors that are inserted into connector 77 and alters its functions accordingly. For example, if controller 78 detects the presence of the conventional ECG electrodes discussed above, the controller disregards the signals from electrodes 21-24 and performs a conventional 12 lead ECG recording that is communicated to the receiving processor. If controller 78 detects a conventional communication bus connected to connector 77, the controller can receive commands from the device at the other end of the communication bus and perform the indicated functions such as updating the software in the ECG data acquisition device.

In one aspect of the invention, ECG data acquisition device 20 includes a compartment 43 that is sized to hold a medication to be taken by the patient if the receiving processor or, a medical facility in communication with the receiving processor, determines that the patient's ECG recordings differ significantly from a reference recordings stored in the receiving device for that patient. For example, if the current ECG recordings differ significantly from the reference recordings the receiving processor could send the recordings to a medical facility that normally treats the patient or contact an emergency unit. If the staff of that facility determines that the patient is at risk for a cardiac event, the patient would be instructed to take the medication in compartment 43 by activating a predetermined indicator on the ECG data acquisition device or the receiving processor and then proceed to the nearest medical facility that can treat the patient or send an ambulance to the patient's location as determined by a position locating system included in ECG data acquisition device 20 or the receiving processor with which ECG data acquisition device 20 communicates. Early treatment with simple medications has been shown to increase positive outcomes for patients with cardiac events. The medication may be a vascular dilator such as nitroglycerin, or other medication prescribed by the patient's regular physician. In one aspect of the invention, the medication is aspirin. In one aspect of the invention, the compartment is only opened in response to a signal from the receiving processor. If the receiving processor determines that there is a significant change in the patient's ECG recordings and cannot contact the appropriate facility, the receiving processor may be programmed to open the compartment and instruct the patient to go to an emergency ward or similar facility for a checkup. Alternatively, compartment 43 can be opened manually, and the receiving processor provides instructions to the user to open the compartment and take the medication.

The above-described embodiments require that the ECG data acquisition device measure the signals from the left and right hands by measuring the signals from electrodes 22 and 23 described above. Providing a reproducible pressure and contact area between the finger and the electrodes has been found to significantly improve the measured signals. In one aspect of the invention, the electrodes include ridges or other structures that engage the bone of the user's finger if the user pushes on the electrode with a force greater than some predetermined force.

Figure 8B:
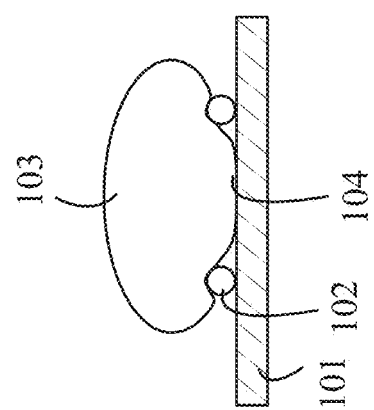
FIGS. 8A and 8B illustrates one embodiment of a finger electrode that can be utilized with the present invention.
Figure 8A:
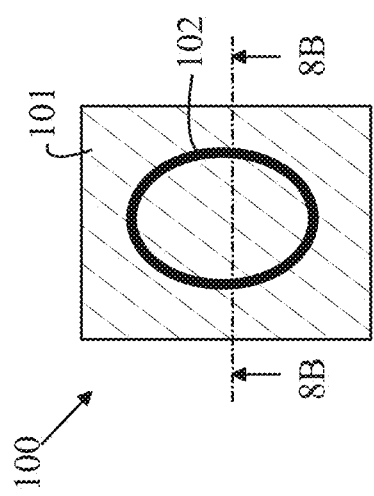

Refer now to FIGS. 8A and 8B, which illustrates one embodiment of a finger electrode that can be utilized with the present invention. FIG. 8A is a top view of electrode 100, FIG. 8B is cross-sectional view of electrode 100 through line 8B-8B. Electrode 100 includes an electrically conducting region 101 that is connected to the electronics that measure the signals from the user's finger. An insulating finger support such as insulating ridge 102 supports the user's finger 103 such that the pad 104 of the finger makes contact with contact area 101. If the user increases the pressure on insulating ridge 102 in an attempt to increase the pressure between pad 104 and electrically conducting region 101, the ridge engages the bone in the user's finger and prevents the finger from moving further toward electrically conducting region 101. As a result, the pressure between the pad and the electrode as well as the area of contact is approximately constant after the applied force of the finger on the electrode structure exceeds some predetermined force. Accordingly, as long as the user presses the user's finger on the electrode with a sufficient force, a reproducible contact area and force is achieved.

It should be noted that insulating ridge 102 can be constructed from a ring of material that is glued onto electrically conducting region 101. The dimensions of the ring can be adjusted for the particular patient for whom the ECG data acquisition device is being provided. The customizable dimensions include the horizontal spacing of the ridge and the height of the ridge. Increasing the height of the ridge increases the minimum pressure with which the patient must press on the electrode structure. The spacing of the ridge is determined by the size of the patient's finger.

While the finger support shown in FIGS. 8A and 8B utilizes an insulating ridge that is attached to the conducting area that is part of the electrode structure, other arrangements for controlling the contact area and contact pressure between the patient's finger and the electrode that measures the ECG signals could be utilized. The important feature of the finger support is that it reduces the variation in the contact area and contact pressure between the patient's finger and the electrode as a function of the force with which the patient presses on the electrode structure.

As noted above, common mode noise is a significant problem in ECG recordings. One method for further reducing this noise in the standard leads is to always form the difference of two signals at different points on the patient body. In the prior art, the standard leads are computed by measuring the signals discussed above with reference to Eqs. (1). In one aspect of the present invention, it has been found experimentally that reduced noise equivalent traces to those shown in Eqs. (1) can be obtained by first measuring the difference between the signals on each of the limbs in question relative to Wilson Central Terminal and then computing leads I, II, and III from these measurements. In the conventional standard lead measurements, lead II is measured as the difference between the potential on an electrode connected to the left leg and an electrode connected to the right hand, and Lead 1 is measured as the difference between the potential on an electrode connected to the left hand and an electrode connected to the right hand.

In this aspect of the invention, the signals from electrodes 22-24 are combined to provide the Wilson Central Terminal signal and the difference between the potential on this combined terminal and each of electrodes 22-24 is then measured. The lead I, II, and III signals are then constructed from these measured signals. Denote the sum of the potentials on electrodes 22-24 by $$V_W = (V_{22} + V_{23} + V_{24})/3$$

Where $V_{22}$, $V_{23}$, and $V_{24}$ are the potentials on electrodes 22-24. Denote the measured difference between $V_W$ and $V_{23}$ by $V_{LH}$, The measured difference between $V_W$ and $V_{22}$ by $V_{RH}$, and the measured difference between $V_W$ and $V_{24}$ by $V_{LG}$. In general, these measured differences will also depend on a gain factor A. Hence, at channels outputs:

$$V_{LG}=A*(V_{24}-V_W)$$

$$V_{RH}=A*(V_{22}-V_W)$$

$$V_{LH}=A*(V_{23}-V_W)$$

By definition, at channels outputs:

$$\text{Lead } I=A*(V_{23}-V_{22})=V_{LH}-V_{RH}$$

$$\text{Lead } II=A*(V_{24}-V_{22})=V_{LG}-V_{RH}$$

$$\text{Lead } III=A*(V_{24}-V_{23})=V_{LG}-V_{LH}$$

Hence, the conventional standard lead traces can be obtained from the measurements that are made relative to the Wilson Central Terminal. As noted above, it has been found experimentally that this arrangement yields standard lead traces that have lower noise.

The above-described embodiments of the present invention have been provided to illustrate various aspects of the invention. However, it is to be understood that different aspects of the present invention that are shown in different specific embodiments can be combined to provide other embodiments of the present invention. In addition, various modifications to the present invention will become apparent from the foregoing description and accompanying drawings. Accordingly, the present invention is to be limited solely by the scope of the following claims.

What is claimed is:

1. An apparatus comprising:
   a handheld device having first, second, third, and fourth electrodes on an outer surface of said handheld device, said handheld device having an extended configuration and a storage configuration;
   a controller that measures signals between said electrodes and provides said signals to another device to generate an ECG recording selected from the group consisting of standard lead traces and precordial traces when said handheld device is in said extended configuration and said first and second electrodes contact a first hand of a patient such that said first and second electrodes contact different locations on said first hand, said third electrode being in contact with a location on said patient's other hand and said fourth electrode contacts a point on said patient's body chosen from the group consisting of said patient's lower abdomen, one of said patient's legs, and a precordial measurement point on said patient, said point depending on said ECG recording; and
   a circuit that generates a common mode cancellation signal from signals on said second, third, and fourth electrodes and couples said common mode cancellation signal to said first electrode during said signal measurements.

2. The apparatus of claim 1 wherein said controller measures signals for one of said precordial lead traces by measuring a difference between a sum of potentials on said second and third electrodes and a potential on said fourth electrode.

3. The apparatus of claim 1 comprising a wireless communication link that transmits said measured signals to said another device, said another device being external to said handheld device.

4. The apparatus of claim 3 wherein said wireless communication link comprises a satellite communication system.

5. The apparatus of claim 1 wherein said another device comprises a vehicle computer that is part of an automobile.

6. The apparatus of claim 1 wherein said handheld device in said storage configuration is too small to allow said patient to contact said first, second, third, and fourth electrodes in a manner that allows said ECG recordings to be made.

7. The apparatus of claim 1 wherein said handheld device is characterized by a maximum dimension and wherein said maximum dimension is less than 7 cm when said handheld device is in said storage configuration and greater than 12 cm when said handheld device is in said extended configuration.

8. The apparatus of claim 1 wherein said handheld device comprises a compartment for storing medication.

9. The apparatus of claim 8 wherein said compartment opens in response to signals from said controller.

10. The apparatus of claim 8 further comprising an indicator that signals that a user should open said compartment and take said medication.

11. The apparatus of claim 1 wherein said handheld device comprises a data input device for receiving input from a user thereof.

12. The apparatus of claim 11 wherein said data input device comprises a plurality of buttons that allow a user to input information.

13. The apparatus of claim 1 comprising a connector configured to receive a plurality of conventional ECG electrodes, said apparatus providing a conventional 12 lead ECG measurement when said ECG electrodes are connected to said connector.

14. The apparatus of claim 13 wherein said connector accepts a cable that connects said device to a charging device for charging batteries in said apparatus and that communicates control signals to said controller.

15. The apparatus of claim 14 wherein said control signals provide patient specific data to be stored in said apparatus.

16. The apparatus of claim 14 wherein said control signals provide software updates to said controller.

17. The apparatus of claim 1 wherein one of said second and said third electrodes comprises an electrically conducting region and an insulating finger support that engages one of said patient's fingers when said patient presses on that electrode, said insulating finger support reducing variations in a contact area and a contact pressure between the patient's finger and said electrically conducting region as a function of a force applied to that electrode by said patient.

18. The apparatus of claim 17 wherein said insulating finger support comprises an electrically insulating ridge attached to said electrically conducting region.

* * * * *